United States Patent [19]
Steiner

[11] Patent Number: 5,236,568
[45] Date of Patent: Aug. 17, 1993

[54] APPARATUS FOR DETERMINING THE PH OF LIQUIDS

[75] Inventor: Ingo Steiner, Eltville, Fed. Rep. of Germany

[73] Assignee: Hoechst Aktiengesellschaft, Frankfurt am Main, Fed. Rep. of Germany

[21] Appl. No.: 754,672

[22] Filed: Sep. 4, 1991

[30] Foreign Application Priority Data

Sep. 15, 1990 [DE] Fed. Rep. of Germany ........ 4029321

[51] Int. Cl.$^5$ .......................................... G01N 27/416
[52] U.S. Cl. ................. 204/406; 204/153.21; 204/408; 204/433
[58] Field of Search .................... 204/433, 152.21, 406, 204/408, 409

[56] References Cited

U.S. PATENT DOCUMENTS

| | | | |
|---|---|---|---|
| 2,563,062 | 8/1951 | Perley | 204/433 X |
| 3,681,205 | 8/1972 | Ducksbury et al. | 204/153.21 |
| 3,839,162 | 10/1974 | Ammer | 204/1 T |
| 3,862,895 | 1/1975 | King et al. | 204/195 |
| 4,154,660 | 5/1979 | Micko | 204/153.21 |

FOREIGN PATENT DOCUMENTS

| | | |
|---|---|---|
| 316901 | 11/1973 | Austria . |
| 0068025 | 1/1983 | European Pat. Off. . |
| 22627 | 1/1960 | German Democratic Rep. . |
| 226080 | 8/1985 | German Democratic Rep. . |

OTHER PUBLICATIONS

R. Brdicka, "Principles of Physical Chemistry", 1963, p. 626.
R. Brdicka, "Principles of Physical Chemistry", 1963, p. 612.
R. Brdicka, "Principles of Physical Chemistry", 1963, pp. 615-618.

*Primary Examiner*—John Niebling
*Assistant Examiner*—William T. Leader
*Attorney, Agent, or Firm*—Foley & Lardner

[57] ABSTRACT

A method for determining the pH of liquids by a pH difference measurement of a solution under test and a reference solution and an apparatus for determining the pH of liquids is provided which can determine the pH with a precision equal to or better than 0.001 pH. The method and apparatus are especially useful for determining the pH and development speed of developers for positive photoresists.

8 Claims, 2 Drawing Sheets

APPARATUS FOR DETERMINING THE PH OF LIQUIDS

BACKGROUND OF THE INVENTION

The invention relates to a method for determining the pH of liquids by a pH difference measurement on a solution under test, and also to an apparatus for determining the pH of liquids.

It is presently possible to measure absolute pH of liquids with a precision of about 0.01 pH. This applies particularly in measurements of alkaline solutions since the glass electrodes used in the measurement have an alkali error of 0.05 pH, for example in a 0.1N NaOH solution, which cannot be calibrated.

In the prior art processes, the pH is determined, for example, with the aid of hydrogen electrodes (Grundlagen der physikalischen Chemie (Principles of physical chemistry), 4th edition, 1963, author: Brdicka, page 626). In this process, the potential of a hydrogen electrode in a solution having any pH value is determined with the aid of a reference electrode. In order to reduce to a minimum the diffusion potential at the interface of diverse electrolytes, the electrode solutions are separated by a bridge. The reference electrode used is, for example, a saturated calomel electrode. If solutions of different concentrations are in contact through a porous wall or a permeable membrane or directly in contact, an electrical double layer forms at their interface, so that a potential drop is produced between the two solutions. This electrical double layer forms as a consequence of the diffusion of the electrolyte out of the concentrated solution into the dilute solution. If the cations and anions of the respective electrolyte have a different mobility, the more mobile type of ion tends to advance quickly in the diffusion. However, the electrostatic forces acting between the oppositely charged ions prevent the independent diffusion of both types of ions and, consequently, the more mobile ions are retarded in their diffusion by the less mobile ions, and, conversely, the diffusion of the slower ions is accelerated by the more mobile ions. The tendency of the more mobile ions to diffuse more rapidly is manifested in the fact that said more mobile ions form a layer of similar charges which is immediately followed by a layer composed of the slower ions with opposite charge, which results in the formation of the electrical double layer. This produces a potential change at the liquid interface. In general, concentration chains having such a potential change between solutions in contact are described as concentration chains with transfer (Grundlagen der physikalischen Chemie (Principles of physical chemistry), 4th edition, Brdicka, page 612).

In determining the electromotive force of concentration chains, the diffusion potential at the interface of the solutions of different concentrations can be suppressed by connecting the electrode solutions by means of a saturated solution of potassium chloride or ammonium chloride. Such a connection is described as a bridge, and instead of one interface between the electrolytes, two interfaces are produced resulting in substantial elimination of the potential drop between the electrolytes.

Calomel electrodes are used as reference electrodes for determining the potential of other electrodes because of their completely reproducible potential. For practical measurement purposes, depending on the requirement, the calomel electrodes are filled with either a 0.1N, 1N or saturated potassium chloride solution as electrolyte bridge.

Using the calibrated reference electrodes or calomel electrodes and a pH-sensitive electrode, for example, a glass electrode, the absolute pH of the electrolytes can be determined by comparison with buffered standard solutions.

In many cases, however, a pH difference measurement in which the solution to be examined is compared with a known or arbitrarily chosen reference solution as standard is sufficient.

SUMMARY OF THE INVENTION

An object of the invention is to provide a method for determining the pH of liquids by a pH difference measurement with a precision equal to or better than about 0.001 pH.

This object is achieved by providing a method wherein the pH difference measurement is carried out by means of glass electrodes between a volume of the solution under test and a volume of a reference solution which has a comparable composition to the solution under test, wherein the reference solution and the solution under test are electrically connected to one another via at least one diaphragm, wherein a grounded metal electrode forms the electrical zero point of a measuring apparatus, and wherein the potential difference between the solution under test and the reference solution is a measure of the difference in the pHs between the two solutions.

It is a further object to provide an apparatus for determining the pH of liquids by a pH difference measurement wherein a reference cell and a measuring cell are electrically connected to one another via a diaphragm, wherein a reference electrode and a measuring electrode are respectively disposed in the reference cell and the measuring cell, and wherein a grounded metal electrode is immersed in a reference solution in the reference cell.

There is further provided an apparatus which has an external vessel which contains an electrolyte solution and wherein a reference cell and a measuring cell are immersed in the electrolyte solution, wherein the reference cell and the measuring cell each have a diaphragm which prevents the liquid exchange between the liquids in the cells and the electrolyte solution, wherein a reference electrode and a measuring electrode are respectively disposed in the reference cell and measuring cell, and wherein a metal electrode which is immersed in the electrolyte solution is grounded.

Further objects, features and advantages of the present invention will become apparent from the detailed description of preferred embodiments that follows.

DETAILED DESCRIPTION OF THE PREFERRED EMBODIMENTS

The invention achieves the advantages that, for a measured value of 0.001 pH, a readily measurable potential difference of 60 μV is obtained in the case of measurements without transfer or 20 μV in the case of measurements with transfer, and that a temperature constancy of the apparatus or of the method of better than 0.05K can be maintained if glass electrodes are used.

In a preferred method, the reference solution and the solution under test are each electrically connected via a diaphragm to an electrolyte solution which forms the electrical zero point of the measuring apparatus and in which the metal electrode is immersed.

The method preferably is carried out in a way wherein the reference solution is not replaced during the measurement and the solution under test is replaced at constant time intervals during the measurement. Under these circumstances, the electrolyte solution is kept at constant temperature and flows uniformly through the measuring apparatus.

The invention is explained in greater detail with reference to two exemplary embodiments shown in the diagrams.

Figure 1:
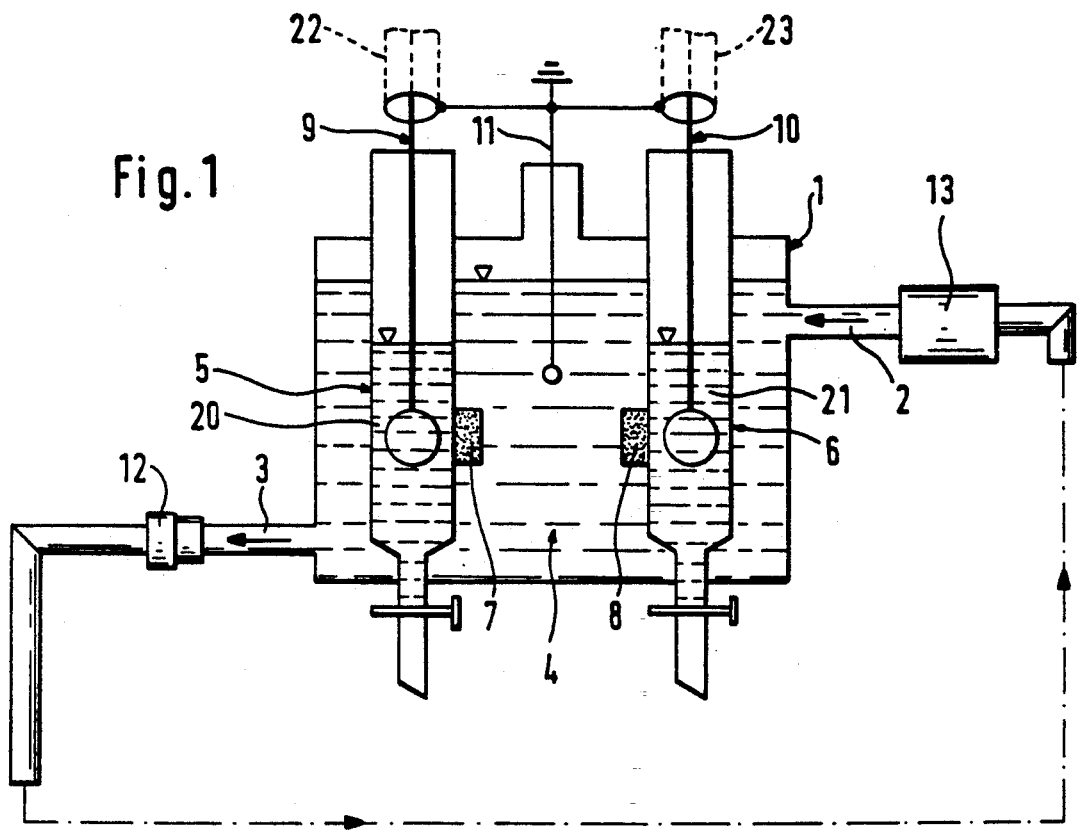
FIG. 1 diagrammatically shows a first embodiment of the measuring apparatus according to the invention, FIG. 2 diagrammatically shows a second embodiment of the measuring apparatus according to the invention.

The first embodiment, shown diagrammatically in FIG. 1, of a measuring apparatus according to the invention, comprises an external vessel 1 which contains an electrolyte solution 4. Situated in the external vessel 1 are a reference cell 5 and a measuring cell 6 which are immersed in the electrolyte solution 4. The reference cell 5 and the measuring cell 6 comprise commercial glass electrodes such as those supplied by the company of Schott, Mainz. At the reference cell and the measuring cell there are diaphragms 7 and 8 which separate the reference solution 20 and the solution under test 21 from the electrolyte solution 4. Since the electrolyte solution is situated between the test and reference solutions, this embodiment is referred to as a measuring arrangement without transfer, in contrast to the second embodiment according to FIG. 2 which is a measuring arrangement with transfer. The diaphragms 7 and 8 prevent the liquid exchange between the liquids in the reference cell and the measuring cell, on the one hand, and the electrolyte solution 4, on the other hand. Furthermore, the measuring apparatus has a metal electrode 11, which is preferably a platinum electrode, which is immersed in the electrolyte solution 4 and is grounded.

The measuring arrangement is of symmetrical construction with reference to said metal electrode 11. The only deviation from this symmetry is in the differences between the reference solution 20 and the solution under test 21.

The external vessel 1 is equipped with an inlet 2 and with an outlet 3 for the electrolyte solution 4 which is circulated by pumping by means of a pump 12 which is in the outlet. Shortly before the inlet 2 into the external vessel 1, there is a thermostat 13 through which the pipe through which the electrolyte solution 4 is pumped is passed. The thermostat 13 ensures a substantially constant temperature of the electrolyte solution 4 which flows through the external vessel 1.

An electrical screen 22 surrounds the reference electrode 9, while the measuring electrode 10 is enclosed by a screen 23. The two screens 22 and 23 are connected to ground together with the metal electrode 11. Via the metal electrode 11, the electrolyte solution 4, also described as an electrolyte bridge, is at ground potential and consequently forms a low-resistance electrical screen for the reference cell 5 and the measuring cell 6.

The reference electrode 9 and the measuring electrode 10 are each glass electrodes of identical construction which have, for example, a central connecting wire of thallium amalgam as electrode. Both the reference electrode and the measuring electrode are connected to the two inputs of a differential amplifier 16 of an amplifier circuit 14 (see FIG. 3), the output of the differential amplifier being connected to a strip chart plotter 15.

The grounded metal electrode 11 is the electrical zero point of the measuring apparatus. As a result of the fact that the screens 22 and 23 of the electrodes 9 and 10, together with the metal electrode 11, are at ground, the measuring apparatus is completely screened against external electromagnetic interferences by the electrolyte solution 4 and the metal electrode 11.

Figure 2:
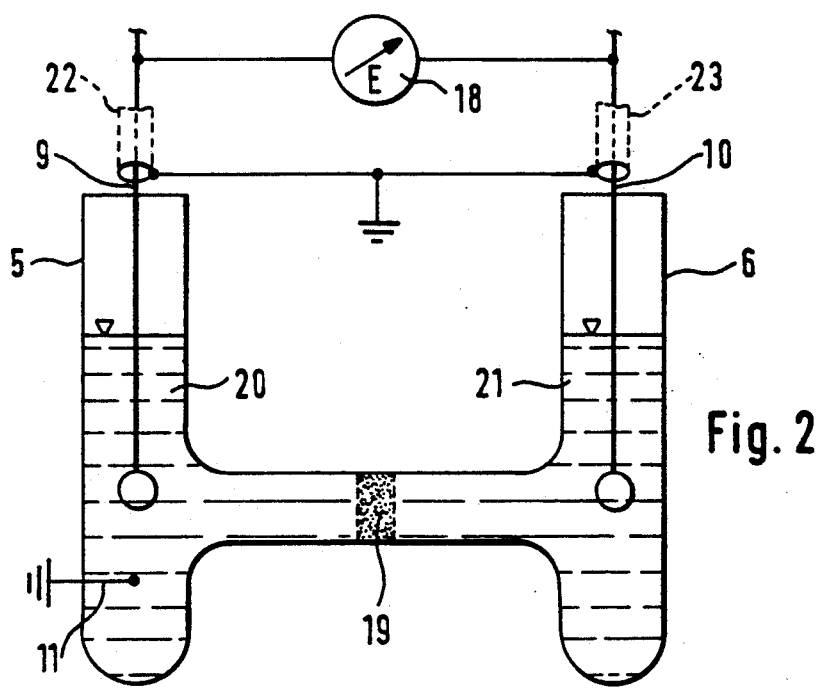

FIG. 2 diagrammatically shows a second embodiment of the measuring apparatus which is a measuring apparatus with transfer having only one diaphragm 19 between the reference solution 20 and the sample solution 21. In FIG. 2, the reference electrode 9 and the measuring electrode 10 are disposed centrally in the reference cell and the measuring cell, respectively. An electrolyte solution as in the first embodiment according to FIG. 1 is not present. 19 is a diaphragm, glass frit, or a porous wall which separates the two different electrolytes, i.e., the reference solution and the sample solution, from one another. The platinum metal electrode 11 is grounded and projects into the lower part of the reference cell. The two electrodes 9 and 10 are connected to a volt meter 18 which indicates the difference voltage between the electrodes, which is also a measure of the pH difference between the reference solution 20 and the sample solution 21. The reference electrode 9 and the measuring electrode 10 may also be connected to an amplifier circuit 14 in conjunction with a strip chart plotter 15, as are described with reference to FIG. 3. The screens 22, 23 of the two electrodes 9, 10 are, like the metal electrode, grounded.

Figure 3:
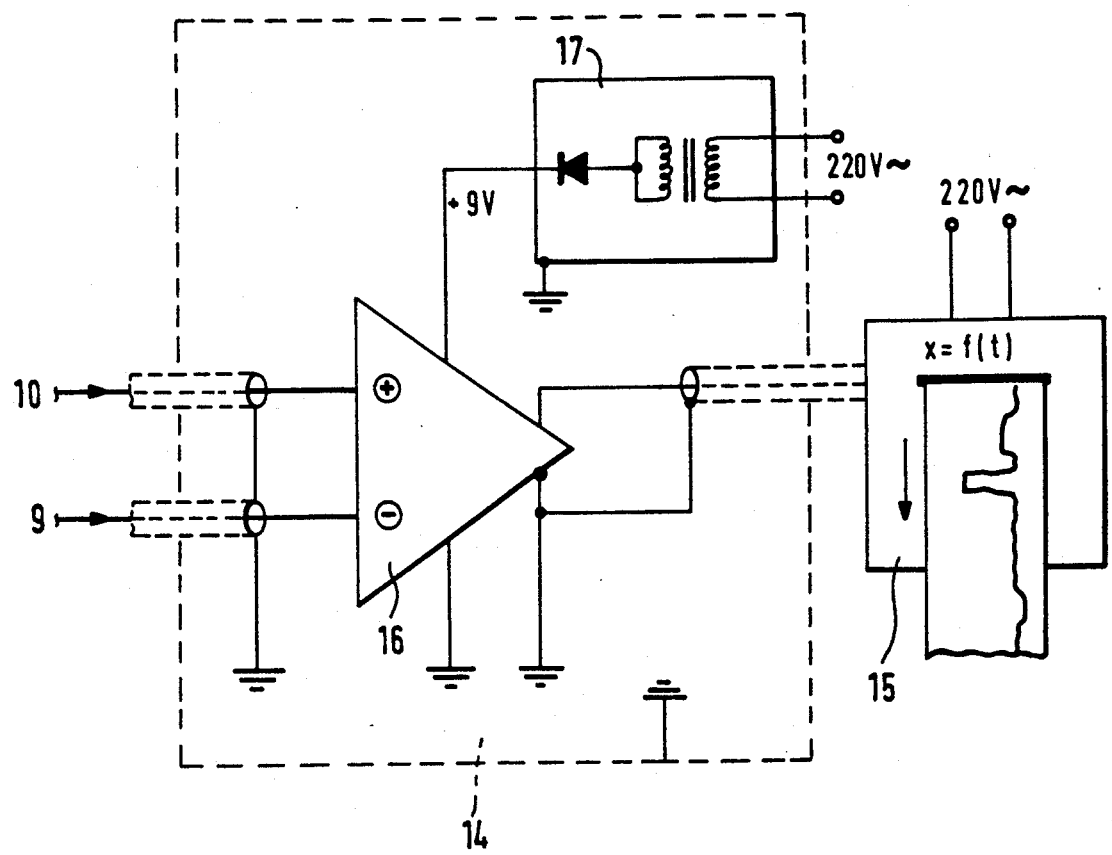
FIG. 3 shows an amplifier circuit and an indicating circuit as a component of the measuring apparatus.

FIG. 3 diagrammatically shows the amplifier circuit 14 and the strip chart plotter 15 connected to the amplifier circuit. The amplifier circuit 14 comprises the differential amplifier 16 which is a high-resistance and low-noise amplifier which has a 3-dB band width of less than about 1 Hz. The input resistance of the differential amplifier 16 is a multiple higher than the electrode resistance of the reference electrode and measuring electrode; each of which is connected to one of the two inputs of the differential amplifier 16. A direct voltage supply 17 supplies the operating voltage for the differential amplifier 16. The output signal of the differential amplifier 16 is fed via a screened cable to an indicating instrument having a resolution of less than or equal to about 10 μV. This indicating instrument is preferably a strip chart plotter 15 which records the variation in the potential difference of the reference solution and the sample solution with time. If the measuring cell according to FIG. 1 without transfer is used, the measured potential difference corresponds to the value of 60 V/0.001 pH to be expected theoretically in accordance with the Nernst equation. The thermal noise voltage due to the resistance of the glass electrodes, whose internal resistance is about 1 GΩ, should be smaller than the required measurement precision of 60 μV. According to the formula $U_R = \sqrt{R \cdot k \cdot T \cdot f}$, the thermal noise voltage of the glass electrodes is found to be 2 μV/$\sqrt{Hz}$ for $R = 1$ GΩ, Boltzmann's constant $k = 1.38 \cdot 10^{-23}$ Ws/degree, $T = 298$K and f in Hz. In relation to its band width, the amplifier circuit 14 must be so designed that the noise voltage is less than the actual measured value, i.e., much less than 60 μV in the measuring cell according to FIG. 1, or 20 μV in the measuring cell according to FIG. 2. In designing the measuring apparatuses, it must be borne in mind that the potential of the glass electrodes is temperature-dependent, so that, for example, for a pH=13, the temperature variation is about 0.02 pH/K. So that this temperature dependence is not noticeable during the measurement, a temperature constancy of the electrolyte solution 4, which is kept at constant temperature in the thermostat 13, of less than about 0.05K is required. The very small potential differences occurring in general in the pH difference measurements are in the case of the first embodiment of the measuring apparatus, i.e., in the case of a measurement without transfer, about 60 μV/0.001 pH, and in the case of the second embodiment of the measuring apparatus, i.e., in the case of a measurement with transfer, about 20 μV/0.001 pH.

The electrolyte solution 4 is, for example, an ionic solution whose concentration and nature are chosen so that the diffusion potential of the entire measuring chain is zero or almost zero for a plurality of samples of solutions under test of different concentrations. Thus, the electrolyte solution 4 may be comprised of a KCl solution having a concentration in the range from about 1 mol/l up to saturation. The KCl electrolyte solution may also contain additional constituents of the solution under test in a concentration which renders the measurable potential difference between reference electrode and measuring electrode insensitive to a liquid exchange through the diaphragms between solution under test, reference solution and electrolyte solution.

With the measuring apparatus of the invention, the OH. ion activity of alkaline developers for positive photoresists can be determined with a precision equal to or less than 1%, based on the solubility of the exposed photoresist areas due to the developer. In addition, it is possible to measure a developer solution having a pH of 12 to 14 against a standard developer solution with the measuring apparatus, the developer solution being loaded into the measuring cell 6 in one case pure and in another case contaminated with $CO_2$. The potential difference of the two measurements on the pure and the contaminated developer solution is a measure of the effect of $CO_2$ z on the development speed. These measurement operations are described below with reference to two examples.

EXAMPLE 1

The electrolyte solution 4 in the measuring apparatus according to FIG. 1 is comprised of an aqueous solution of ammonium acetate of concentration 1.95 mol/l.

The reference cell 5 is loaded with a developer solution for positive photoresists which is standard in microelectronics and which consists of an aqueous solution of 0.27 mol/l tetramethylammonium hydroxide (TMAH).

The measuring cell 6 is loaded successively with aqueous TMAH solutions in the concentration range of from 0.24 mol/l to 0.33 mol/l. The potential difference in each case between the reference electrode 9 and the measuring electrode 10 is recorded. If a complete dissociation of the strong base TMAH is assumed, it holds true that:

$$[OH^-] = [TMAH]$$

With the ionic product Kw of water, it holds true in aqueous solution that:

$$[H^+] = K_w/[OH^-]$$
$$= K_w/[TMAH],$$
$$\log[H^+] = \log K_w - \log[TMAH]$$

and with $$pH = -\log[H^+],$$

it follows that $$pH = \log[TMAH] - \log K_w.$$

According to Nernst, the slope of glass electrodes is 59.2 mV/pH at 25° C. If the values obtained from the example for the potential difference U are plotted against the logarithm of the TMAH concentration in the cell 6, a straight line with a slope of $$\frac{U}{\log[TMAH]} = 60.4 \text{ mV}/\log[mol/l]$$

results. The measurement precision is so good that the deviations from this straight line are less than 50 μV. As a result of the chosen electrolyte solution with the large acetate anion compared with the more highly mobile ammonium ion $NH_4^+$, no "transfer" occurs in the measuring apparatus, i.e., the measured potential difference is not reduced by diffusion potentials and corresponds to the theoretical value of 59.2 mV/log [mol/l] with good precision. The diffusion potentials can be calculated in accordance with Henderson (Grundlagen der physikalischen Chemie, 4th edition, Brdicka, pages 615–618). For the chosen example, calculation shows for the specified concentration range that the sum of all the diffusion potentials is less than 40 μV and is consequently insignificant.

The measurement precision of better than 50 μV corresponds to 0.0008 pH units. Based on the TMAH concentration, this implies a precision of 0.0005 mol/l. The correlation with function tests of the developer yields a precision of the developer activity (development rate) of 0.8%.

This precision, which is higher than conventional pH measurements by a power of ten, is achieved by the difference measurement in the first embodiment of the measuring apparatus. In that embodiment, an electrical and chemical compensation of the error values occurs as a result of counterbalanced connection of two cells or electrodes of identical construction. Only the "absolute error" or symmetry error remains as a residual error of the measurement. As a result of electrical screening of the measuring apparatus, interferences and noise remain in the order of magnitude of approximately 20 μV below the measurement precision.

Instead of tetramethylammonium hydroxide, sodium hydroxide and sodium borate, or sodium phosphate and sodium silicate are also suitable developers comprised of an aqueous alkaline solution.

Calibration or buffer solutions for the pH measurement in the alkaline range with a precision of less than or equal to 0.001 pH can also be prepared by the method of the invention.

EXAMPLE 2

The electrolyte solution in the measuring apparatus according to FIG. 1 is comprised of a 3.5 mol/l KCl solution. A buffered developer solution composed of 0.35 mol/l NaOH and 0.254 mol/l boric acid is loaded into the reference cell 5. The same solution is loaded into the measuring cell 6 in one case, then the same solution contaminated with 0.00020 to 0.00026 mol/l $CO_2$ is loaded. The measured potential difference for 0.00026 mol/l $CO_2$ is 90 $\mu V$. The extrapolation of this value to the developer activity implies a deceleration of the development rate by 1.3%. A measurement of such low $CO_2$ concentrations by titration is not possible by the prior processes. Even if the indicated potential difference is only 66% of the theoretical value in this case, which is attributable to residual diffusion potentials in the chosen electrolyte solution, the measuring apparatus makes it possible to measure the developer activities with a precision of better than 1% in all cases.

The measurements make it possible to determine simply and rapidly the developer activity of alkaline developers for developing positive photoresists based on phenolic resin/naphthoquinone diazide by measuring the H. ion activity and the OH-activity thereby given. The basis of this is the order of magnitude of the dependence of the developer activity (developer erosion rate) on the pH of the developer solution. The developer activity A is a function of the pH, a difference in the developer activity of 10% roughly corresponding to a pH difference of 0.01. The absolute pH of a typical alkaline developer solution is in the range $12.5 \leq pH \leq 13.0$. For two main reasons an absolute measurement of the pH was not possible with sufficient reproducibility in this range:

(a) The "alkali error" of glass electrodes, mainly due to $Na^+$ ions, is about 0.05 pH units for good glass electrodes. As already mentioned above, this error cannot be calibrated.

(b) According to the present state of the art, pH absolute measurements have an inherent measurement error in the order of magnitude of 0.01 pH units.

The apparatuses according to the invention eliminate, or compensate for, these effects as far as possible since the measuring apparatuses make possible a difference measurement of the $H^+$ ion activity of the sample solutions and the errors are compensated for by the substantially symmetrical arrangement of the reference electrode and measuring electrode. In the first embodiment of the measuring apparatus, the electrodes are of identical construction and are immersed in a specified electrolyte solution or developer solution. In the second embodiment of the measuring apparatus, the measuring cell and the reference cell are connected in an electrically conducting manner with one another, for example via a glass frit, but are not immersed in an electrolyte solution.

What is claimed is:

1. An apparatus useful for determining the difference of pH-values of liquids by a pH difference measurement technique, comprising;
   a reference cell containing a reference electrode disposed in a reference liquid, said reference cell having a diaphragm;
   a measuring cell containing a measuring electrode disposed in a liquid to be tested, said measuring cell having a diaphragm;
   an external vessel containing an electrolyte solution in which said reference cell and said measuring cell are immersed; and
   a metal electrode immersed in said electrolyte solution, said metal electrode being grounded so that said electrolyte solution is an electrical shield, wherein the diaphragm of the reference cell is adapted to prevent liquid exchange between the reference liquid and the electrolyte solution and the diaphragm of the measuring cell is adapted to prevent liquid exchange between the liquid to be tested and the electrolyte solution.

2. The apparatus as claimed in claim 1, wherein the external vessel has an inlet and an outlet for the electrolyte solution, a pump adapted to circulate the electrolyte solution through the inlet, the eternal vessel and the outlet, and a thermostat through which the electrolyte solution passes to keep the temperature constant, said thermostat being disposed outside the external vessel.

3. The apparatus as claimed in claim 2, additionally comprising a first screen surrounding a first cable connecting the reference electrode to a differential amplifier and a second screen surrounding a second cable connecting the measuring electrode to the differential amplifier, each of said first and second screens being electrically at ground together with the metal electrode.

4. The apparatus as claimed in claim 1, additionally comprising a first screen surrounding a first cable connecting the reference electrode to a differential amplifier and a second screen surrounding a second cable connecting the measuring electrode to the differential amplifier, each of said first and second screens being electrically at ground together with the metal electrode.

5. The apparatus as claimed in claim 1, wherein the reference electrode and the measuring electrode are each glass electrodes of identical construction and have a central connecting wire of thallium amalgam or calomel, and wherein the reference and measuring electrodes are connected to two inputs of a differential amplifier whose output is connected to a strip chart plotter.

6. The apparatus as claimed in claim 5, wherein the amplifier is a high-resistance and low-noise differential amplifier which has a 3-dB band width of less than about 100 Hz, and wherein the output signal of the differential amplifier is applied to an indicating instrument having a resolution of less than or equal to about 10 $\mu V$.

7. The apparatus as claimed in claim 6, wherein the input resistance of the differential amplifier is a multiple higher than the electrode resistance of the reference electrode and measuring electrode, and wherein the thermal noise voltage due to the electrode resistance is less than the measurement precision of about 60 $\mu V$, which corresponds to a pH of about 0.001.

8. The apparatus as claimed in claim 1, wherein the electrolyte solution is comprised of a KCl solution having a concentration in the range of from about 1 mol/l up to saturation.

* * * * *